US010219722B2

(12) United States Patent
Tanttu

(10) Patent No.: US 10,219,722 B2
(45) Date of Patent: Mar. 5, 2019

(54) MRI THERMAL IMAGING OF WATER TISSUE AND FAT TISSUE USING TRANSVERSE RELAXOMETRY DATA AND PROTON RESONANCE FREQUENCY SHIFT DATA

(75) Inventor: Jukka Ilmari Tanttu, Espoo (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1244 days.

(21) Appl. No.: 13/817,912

(22) PCT Filed: Aug. 26, 2011

(86) PCT No.: PCT/IB2011/053752
§ 371 (c)(1),
(2), (4) Date: Feb. 20, 2013

(87) PCT Pub. No.: WO2012/029006
PCT Pub. Date: Mar. 8, 2012

(65) Prior Publication Data
US 2013/0158387 A1 Jun. 20, 2013

(30) Foreign Application Priority Data
Aug. 30, 2010 (EP) ...................................... 10174485

(51) Int. Cl.
*A61B 5/055* (2006.01)
*G01R 33/48* (2006.01)
(Continued)

(52) U.S. Cl.
CPC ................ *A61B 5/055* (2013.01); *A61B 5/01* (2013.01); *A61B 5/4836* (2013.01);
(Continued)

(58) Field of Classification Search
CPC ....... A61B 18/1206; A61B 18/24; A61B 5/01; A61B 5/055; A61B 5/4836; A61B 5/4872;
(Continued)

(56) References Cited

U.S. PATENT DOCUMENTS 4,777,957 A * 10/1988 Wehrli et al. .................. 600/413
5,492,122 A * 2/1996 Button et al. .................. 600/411
(Continued)

FOREIGN PATENT DOCUMENTS

| JP | 2000300591 A | 10/2000 |
|----|--------------|---------|
| WO | 0135825 A1 | 5/2001 |
| WO | 0140819 A1 | 6/2001 |

OTHER PUBLICATIONS

Yuhua Peng, Honghong Dong, Xiaoying Tang. "Noninvasive temperature measurement using MRI based on T2 relaxation time." Bioinformatics and Biomedical Engineering (IDBBE), 2010 4th International Conference, Beijing, China.
(Continued)

*Primary Examiner* — Ruth S Smith

(57) ABSTRACT

An apparatus (300, 400, 500) comprising a magnetic resonance imaging system (302), the magnetic resonance imaging system comprising: a magnet (306) adapted for generating a magnetic field for orientating the magnetic spins of nuclei of a subject (310) located within an imaging volume (308); a radio frequency transceiver (320) adapted for acquiring magnetic resonance data (346) using a radio frequency coil (318); a computer system (336) comprising a processor (338), wherein the computer system is adapted for controlling the apparatus; and a memory (342, 344) containing machine readable instructions (354, 356, 358, 360, 362), wherein execution of the instructions cause the processor to perform the steps of: acquiring (100, 204) magnetic resonance data using the magnetic resonance imaging sys-
(Continued)

tem, wherein the magnetic resonance data comprises transverse relaxometry data, and calculating (102, 206) the temperature of the subject within a temperature measurement volume (332) in accordance with the transverse relaxometry data.

12 Claims, 8 Drawing Sheets

(51) Int. Cl.
*A61B 5/01* (2006.01)
*A61B 5/00* (2006.01)
*A61B 18/12* (2006.01)
*A61B 18/24* (2006.01)
*A61N 7/02* (2006.01)

(52) U.S. Cl.
CPC .......... *A61B 5/4872* (2013.01); *A61B 5/4875* (2013.01); *A61B 5/7278* (2013.01); *A61B 18/1206* (2013.01); *A61B 18/24* (2013.01); *A61N 7/02* (2013.01); *G01R 33/4804* (2013.01); *G01R 33/4828* (2013.01)

(58) Field of Classification Search
CPC ...... A61B 5/4875; A61B 5/7278; A61N 7/02; G01R 33/4804; G01R 33/4828
See application file for complete search history.

(56) References Cited

U.S. PATENT DOCUMENTS

| | | | | |
|---|---|---|---|---|
| 5,508,612 | A * | 4/1996 | Kanazawa | 324/309 |
| 6,032,068 | A * | 2/2000 | Daniel et al. | 600/412 |
| 6,315,981 | B1 * | 11/2001 | Unger | 424/9.323 |
| 6,618,608 | B1 | 9/2003 | Watkins | |
| 6,618,620 | B1 * | 9/2003 | Freundlich et al. | 607/27 |
| 7,542,793 | B2 | 6/2009 | Wu et al. | |
| 8,311,609 | B2 | 11/2012 | Harvey et al. | |
| 2004/0039280 | A1 * | 2/2004 | Wu et al. | 600/412 |
| 2008/0086050 | A1 * | 4/2008 | Misic et al. | 600/411 |
| 2009/0088623 | A1 * | 4/2009 | Vortman et al. | 600/411 |

OTHER PUBLICATIONS

K.M. Johnson, V. Chebrolu, S.B. Reeder. "Absolute Temperature Imaging with Non-Linear Fat/Water Signal Fitting." International Society for Magnetic Resonance in Medicine proceedings, 16th Scientific Meeting. Toronto, Canada 2008.

Viola Rieke, PhD, Kim Ubtts Pauly, PhD. "MR Thermometry." Journal of Magnetic Resonance Imaging 27:376-390 (2008).

S.M. Sprinkhuizen, C.J. Bakker, L.W. Bartels. "Absolute MR Thermometry using time domain analysis of the multi gradient-echo modulus signal." Magn Reson Med. Jul. 2010;64(1):239-48. doi: 10.1002/mrm.22429.

Janaka P. Wansapura, Bruce L. Daniel, John Pauly, Kim Butts. "Temperature Mapping of Frozen Tissue Using Eddy Current Compensated Half Excitation RF Pulses." Magnetic Resonance in Medicine 46 985-992 (2001).

S. Gandhi, B.L. Daniel, K. Butts. "Temperature Dependence of Relaxation Times in Bovine Adipose Tissue." Sanford, CA. DOI 10.1002/mrmp22419980115. Proceedings of the International Society for Magnetic Resonance in Medicine. pp. 701-750. Sydney, Australia, 1998.

Kullervo Hynynen, Nathan McDannold, Robert V Mulkern, Ferenc A. Jolesz. "Temperature monitoring in fat with MRI." Magnetic Resonance in Medicine, vol. 43, Issue 6, pp. 901-904, Jun. 2000.

Chen, X., Barkauskas, K. J., Nour, S. G., Duerk, J. L., Abduli-Karim, F. W. and Saidel, G. M. (2007), Magnetic resonance imaging and model prediction for thermal ablation of tissue. J. Magn. Reson. Imaging, 26: 123-132. doi: 10.1002/jmri.20956.

Damianou C, Ioannides K, Hadjisavvas V, Mylonas N, Couppis A, Iosif D. In vitro and in vivo brain ablation created by high-intensity focused ultrasound and monitored by MRI. IEEE Trans Ultrason Ferroelectr Freq Control. Jun. 2009;56(6):1189-98. doi: 10.1109/TUFFC.2009.1160.

Larrat, B et al. MR Guidance, monitoring and control of Brain HIFU therapy in small animals: In vivo demonstration in rats at 7T. Ultrasonics Symposium (2009) IEEE International, pp. 204-207.

Baron et al, In Vivo T2 Based MR Thermometry in Adipose Tissue Layers for High Intensity Focused Ultrasound Near-Field Monitoring' Magnetic Resonance in Medicine, 72: p. 1057-1064.

Rieke et al "MR Thermometry" Journal of Magnetic Resonance Imaging vol. 27 p. 376-390 (2008).

\* cited by examiner

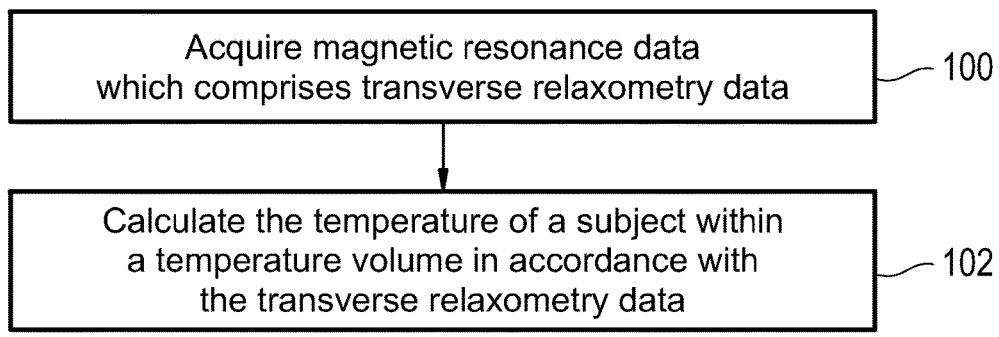
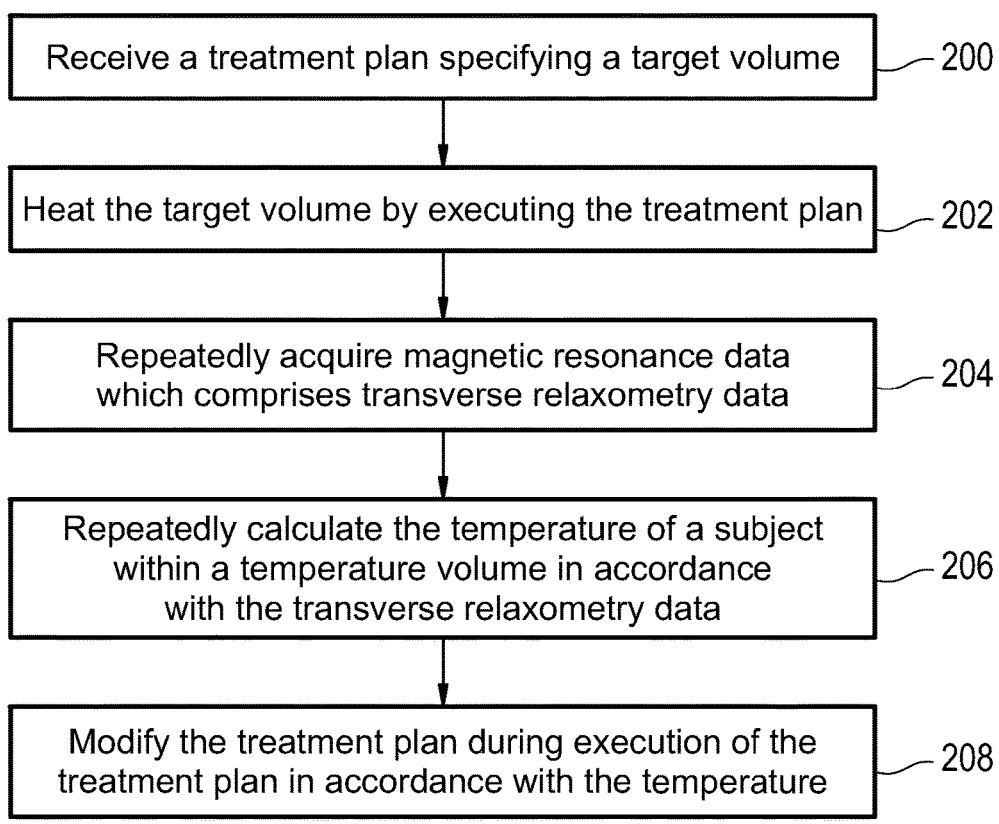

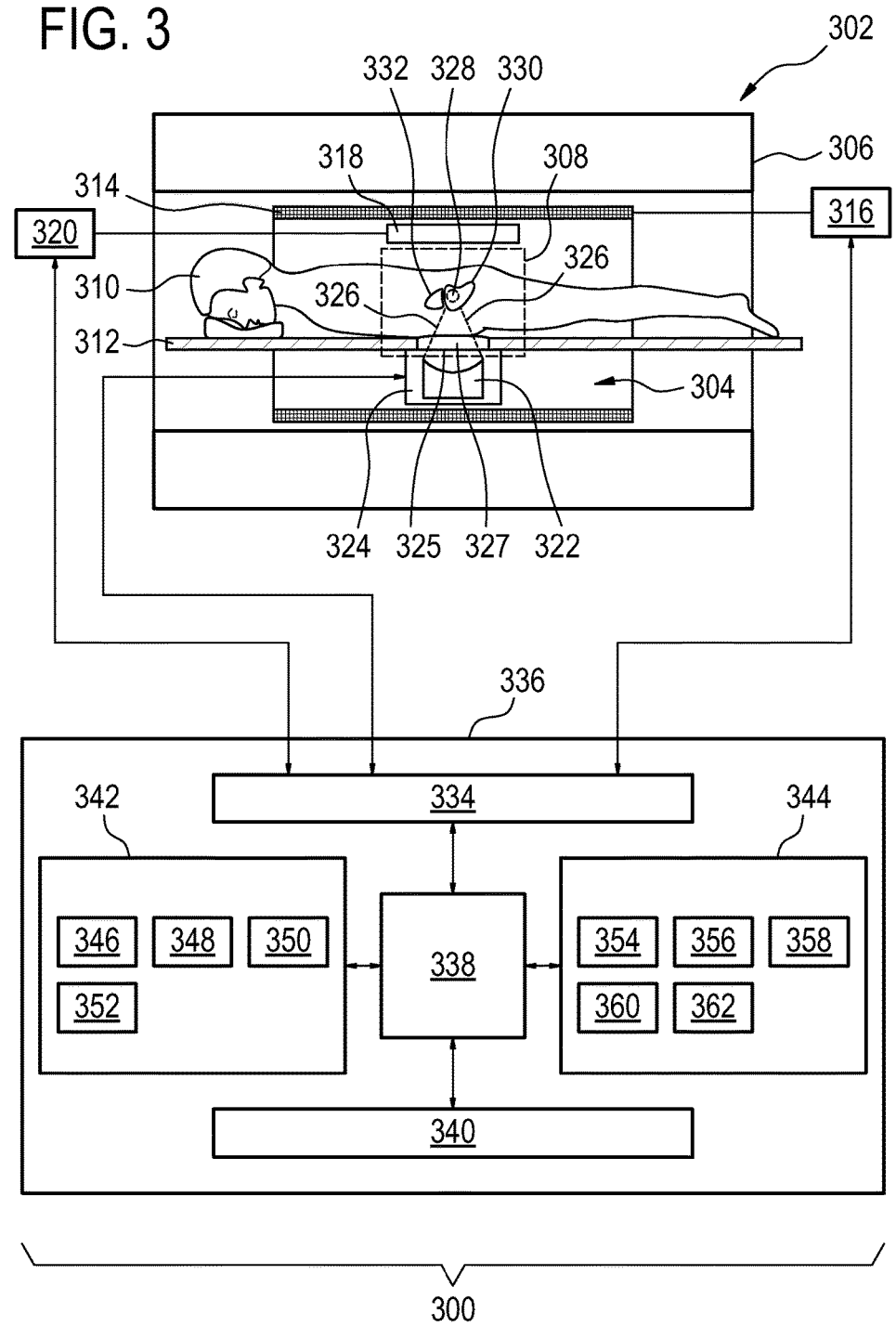

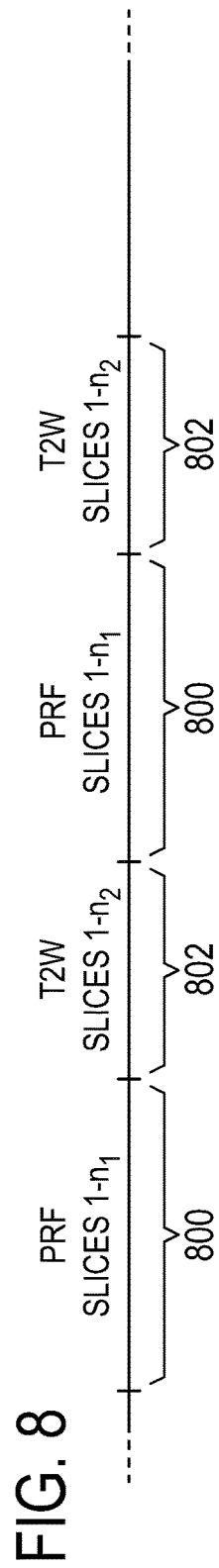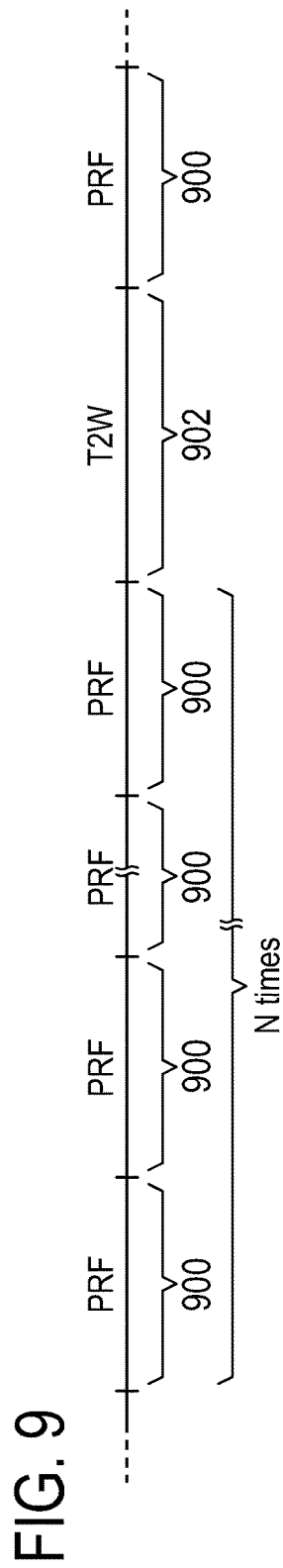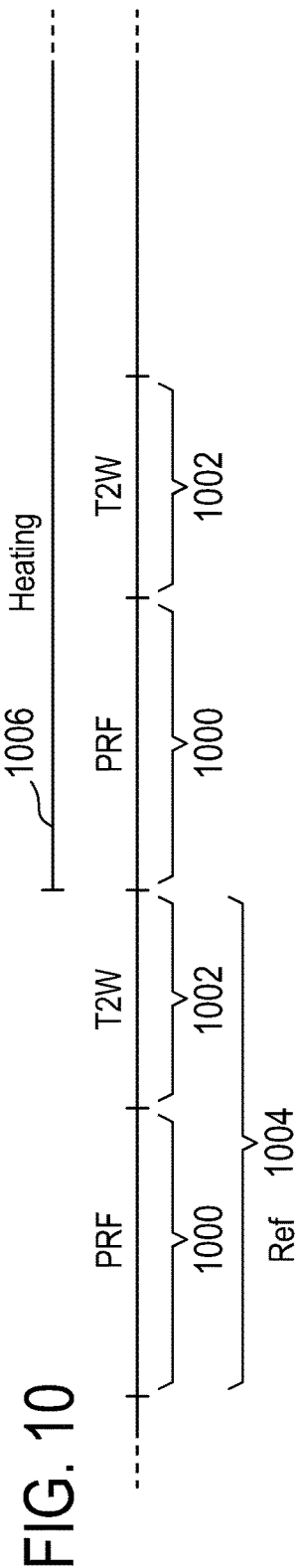

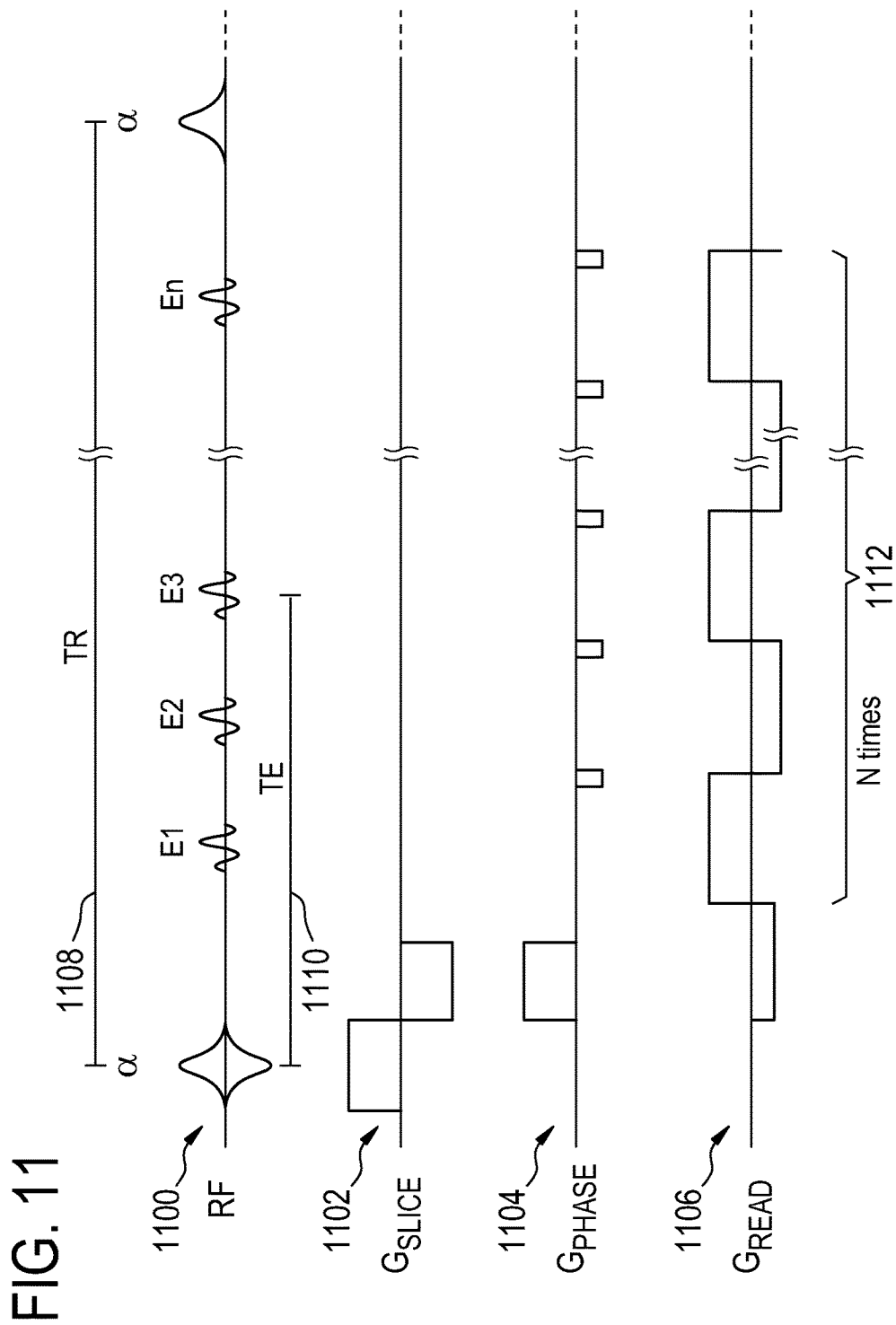

MRI THERMAL IMAGING OF WATER TISSUE AND FAT TISSUE USING TRANSVERSE RELAXOMETRY DATA AND PROTON RESONANCE FREQUENCY SHIFT DATA

TECHNICAL FIELD

The invention relates to magnetic resonance imaging, in particular to the calculation of temperature using transverse relaxometry data.

BACKGROUND OF THE INVENTION

The localized heating of tissues may be useful for therapeutic treatments. For example increased tissue temperature may be used to induce necrosis or induce other physiological changes in the target tissue. There exists a variety of means for localized heating of tissue. High Intensity Focused Ultrasound (HIFU), the ablation of tissue with lasers, and the heating of tissue with electromagnetic fields are some examples of how tissue may be heated locally.

When heating tissue locally, it is beneficial to either measure the temperature of the region being heated and/or tissue surrounding the tissue being heated. For instance, during a HIFU procedure it may be beneficial to monitor the temperature of surrounding tissue to ensure that damage to sensitive organs or tissue does not result.

Magnetic resonance imaging has been combined with HIFU to monitor the heating effect caused by HIFU. The combination of magnetic resonance imaging and HIFU is also beneficial because the magnetic resonance imaging may be used to provide anatomical data as well as to measure the temperature within a subject.

U.S. Pat. No. 7,542,793 discloses a MRI system used to guide an ultrasonic transducer at tissues to be treated and to produce images which enable the treatment of tissues to be monitored. Changes in amplitude of a spin-echo NMR signal from a reference spin-echo NRM signal are used to produce image which indicate temperature changes in both fat and water. The method disclosed in this patent is a proton resonance frequency shift (PRF) method of determining the temperature.

SUMMARY OF THE INVENTION

The invention provides for an apparatus, a computer-implemented method, and a computer program product in the independent claims. Embodiments are given in the dependent claims.

A difficulty with the current state of the art is that the PRF method of measuring temperature with magnetic resonance imaging is that the PRF shift in fat is difficult to measure. Fast and effective T1 weighted FFE sequences may be used for the purpose, but their accuracy often suffers from motion artifacts and B1 distortions (especially at 3 Tesla). The results obtained do not produce accurately measure the temperature of fat. However, temperature measurement of fat may be very useful, for example to avoid excessive near field US heating of subcutaneous fat, or monitor the fat close to breast lesions. Today, without practical solutions for fat temperature monitoring, e.g. heating of subcutaneous fat cannot be monitored, which is a safety risk. In the future, there will also be applications where there is often fatty tissue very close to the treated lesion (e.g. breast, bones, etc).

Embodiments of the invention address this problem by using transverse relaxometry. Transverse relaxometry may be interpreted as the measurement of either the T2 or T2-star relaxation rate. Transverse relaxometry data may also be interpreted as the intensity of a T2 or a T2-star weighted image. T2 is the so called spin-spin relaxation rate and is time that atomic spins need to de-phase in the transverse plane. T2-star is a combination of the spin-spin relaxation time plus de-phasing in the transverse plane due to local magnetic field inhomogeneity.

It is not generally understood that the T2 and T2-star of fat have quite significant temperature dependence. This dependence offers possibilities to utilize fast T2 or T2-star dependent sequences for qualitative or quantitative temperature measurement.

For HIFU, it is beneficial if the temporal resolution of the temperature measurement is on the order of a few seconds. For commercial systems presently used in clinical settings the temporal resolution is typically 2 to 3 seconds. Also, the selected method shall be robust enough, e.g. against motion and flow. There are several alternatives for fast and relatively robust T2 or T2-star weighted sequences, like single-shot TSE or single-shot EPI.

Experimental measurements show that both T2 and T2-star of in in-vitro fat samples are temperature dependent. This is also true for some oils that have been used for Magnetic Resonance (MR) or Ultra Sound (US) phantoms. The experimental data also shows that the apparent T2 temperature changes varies when measured with different sequences, indicating that the T2 relaxation mechanisms may depend in different ways on temperature. Especially J-coupling behaves differently compared to other mechanisms. Also, for T2-star weighted sequences there is interference pattern as a function of the Time to Echo (TE) due to the fat NMR spectrum. This pattern might also be temperature dependent.

The T2 relaxation time change of fat seems to be roughly linear within the studied temperature region. It is probable that close to phase transition temperature of fat the T2 dependence becomes very non-linear, and the T2 change is irreversible.

Embodiments of the invention may produce qualitative or quantitative temperature information of fat based on optimized T2 or T2-star weighted sequence. This information can then be combined in applications like HIFU or other MR guided ablation methods. In practice it might be useful to combine PRF and T2 weighted methods to get temperature information from both water and fat-containing tissues.

Typically T2 or T2* weighted sequences depend on other physical, physiological or technical parameters which may not be stable during the whole treatment procedure. Therefore, it may be essential to compare the signal intensity of the sequence with a reference image obtained just before each heating event. Then the temperature information is the temperature change compared the situation before heating. While this information is very useful, it could beneficial to get measurement of the absolute temperature also. Example of such case is the accumulation of the heat in subcutaneous fat after several heating events in HIFU treatment. In those cases measuring the change in T2 or T2-star compared to the situation just before the treatment would provide temperature in more absolute scale.

Embodiments of the invention may involve performing the following steps:
  In MR guided HIFU ablation, PRF sequence is applied during the US treatment.
  In predefined time intervals, a fat-selected single-shot T2 weighted TSE sequence is obtained in one or more slice positions.

The signal intensity obtained is compared to the images done before the treatment Pre-calibrated look-up table is used to convert the signal intensity change in temperature scale The temperature estimate is shown on the images, for example as a color overlay to indicate to the user of possible safety hazard There are numerous variations of the invention. Some of basic elements of the methods are listed below:

Utilization of T2 temperature dependence of fat for qualitative or quantitative temperature mapping in HIFU or other ablation experiment with T2 weighted sequences like multi-shot or single-shot TSE, multi-shot or single-shot GRASE, spine echo, spin echo EPI.

Utilization of T2-star temperature dependence of fat for qualitative or quantitative temperature mapping with T2-star weighted sequences like FFE, or field echo EPI.

Combine T2-star dependence and temperature dependent shift of fat and water peaks for qualitative or quantitative temperature mapping by selecting TE in FFE based sequence in such a way these effects are synergistic.

Use relative long repetition time compared to T1 of the tissue under interest to get optimized T2 weighting in the TSE, GRASE, EPI or FFE sequence. Alternatively or additionally use low excitation flip angle for gradient echo EPI or FFE.

Use single-shot sequence or a sequence with low T1 saturation to avoid the effects due T1 temperature dependence.

Utilize T2 weighted IR sequence in such a way that T1 and T2 or T2-star temperature effects are synergistic. Typically this means that short Inversion Time (TI) and long TE are used.

Combine PRF and T2 dependent sequence sequentially to almost simultaneously obtain data for water and fat containing tissues.

Combine PRF and T2 or T2-star dependent sequences sequentially by using fat selective excitation for the T2 or T2-star weighted sequence and water selective sequence for the PRF measurement. With this arrangement the interference between the sequences due to saturation effects are minimized.

Use predefined function or look-up table to convert the intensity data of T2 or T2-star dependent sequence to estimated temperature data. This look-up table or function can take to account other temperature dependent factors (like magnetization or T1).

Obtain images with several TE values to get quantitative T2 estimation. This would allow more absolute temperature scale.

Embodiment of the invention may be used in MR applications where the temperature monitoring of tissue is essential. Examples of such are MR guided HIFU, MR guided RF ablation, or MR guided laser ablation.

A computer-readable storage medium as used herein is any storage medium which may store instructions which are executable by a processor of a computing device. The computer-readable storage medium may be a computer-readable non-transitory storage medium. The computer-readable storage medium may also be a tangible computer readable medium. A computer-readable storage medium may also be referred to as 'memory.' In some embodiments, a computer-readable storage medium may also be able to store data which is able to be accessed by the processor of the computing device. An example of a computer-readable storage medium include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

Computer memory is an example of a computer-readable storage medium. Computer memory is any memory which is directly accessible to a processor. Examples of computer memory include, but are not limited to: RAM memory, registers, and register files.

Computer storage is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

Magnetic resonance data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic resonance thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry is enabled by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

In one aspect the invention provides for an apparatus comprising a magnetic resonance imaging system. The magnetic resonance imaging system comprises a magnet adapted for generating a magnetic field for orienting the magnetic spins of nuclei of a subject located within an imaging volume. An imaging volume as used herein encompasses a region of the magnetic field of the magnet which is uniform enough for performing the acquisition of magnetic resonance imaging data. The magnetic resonance imaging system further comprises a radio frequency transceiver adapted for acquiring magnetic resonance data using a radio frequency coil. It is understood herein that the radio frequency transceiver may also be a separate radio frequency transmitter and a separate radio frequency receiver. Likewise a radio frequency coil also encompasses separate transmit and receive coils or antennas. The magnetic resonance imaging system further comprises a magnetic field gradient coil adapted for spatial encoding of the magnetic spins of nuclei within the imaging volume. The term magnetic field gradient coil encompasses all or a collection of magnetic field gradient coils. Typically magnetic resonance imaging systems have three separate gradient coil systems.

The magnetic resonance imaging system further comprises a magnetic field gradient coil power supply for supplying current to the magnetic field gradient coil. When the magnetic field gradient coil power supply supplies current to the magnetic field gradient coil the magnetic field gradient coil generates a magnetic field. The magnetic resonance imaging system further comprises a computer system comprising a processor. The computer system is adapted for controlling the apparatus. That is to say the computer system functions as a control system for the apparatus. It is understood that a computer system and a processor may actually be comprised of multiple computer systems and/or multiple processors. The magnetic resonance imaging system further comprises a memory containing machine readable instructions for execution by the processor. Execution of the instructions cause the processor to perform the step of acquiring magnetic resonance data using the magnetic resonance imaging system. The magnetic resonance data comprises transverse relaxometry data. Transverse relaxometry data as used herein encompasses data which can be used to infer or calculate the T2 or T2-star relaxation time or the signal intensity of T2 or T2-star weighted images.

Execution of the instructions further cause the processor to perform the step of calculating the temperature of the subject within a temperature measurement volume in accordance with the transverse relaxometry data. The temperature measurement volume is within the imaging volume. Embodiments of this apparatus may be particularly beneficial because transverse relaxometry data is used to calculate the temperature within the temperature measurement volume. This is particularly beneficial when fatty tissue is within the temperature measurement volume. This is because the T2 or T2-star relaxation time may be used to accurately measure the temperature in fatty tissue.

In another embodiment the temperature within the temperature measurement volume is calculated by any one of the following: by determining the change of signal intensity in a T2 weighted magnetic resonance image, by calculating the T2 relaxation time, and by calculating the T2-star relaxation time. This embodiment is advantageous because any of these methods may be used to use the transverse relaxometry data to determine the temperature.

In another embodiment the temperature measurement volume contains fat tissue.

In another embodiment the therapeutic apparatus further comprises a tissue heating system for heating a target volume of the subject. The target volume is within the imaging volume. The computer system is further adapted for controlling the tissue heating system. Depending upon the embodiment the target volume may be identical with the temperature measurement volume or they may be different. For instance a tissue heating system may be used to heat a target volume and the temperature of the target volume may be measured directly with the magnetic resonance imaging system. In other cases the target volume may be heated with a tissue heating system and a volume adjacent to the target volume may be monitored to see or ensure that the temperature measurement volume does not exceed a maximum threshold temperature. For instance a laser system may be used to ablate tissue and the magnetic resonance imaging system may be used to monitor an adjacent volume of tissue. This is particularly beneficial because this can be used to ensure that healthy tissue is not destroyed or damaged during a therapy session.

In another embodiment of the tissue heating system a high intensity focused ultrasound system for sonicating the target volume.

In another embodiment the tissue heating system is a radio frequency tissue heating system for heating the target volume with radio frequency energy.

In another embodiment the tissue heating system is a laser ablation system for ablating tissue within the target volume.

In another embodiment the instructions further cause the processor to perform the step of receiving a treatment plan specifying a target volume within the imaging volume. The treatment plan comprises instructions for controlling the operation of the tissue heating system. A 'treatment plan' as used herein encompasses a set of instructions which may either be interpreted into control signals or are control signals for the tissue heating system.

The instructions further cause the processor to perform the step of heating the target volume using the tissue heating system by executing the treatment plan. Execution of the treatment plan causes the processor to send control signals to the tissue heating system which causes the tissue heating system to heat the target volume. The instructions further cause the processor to perform the step of repeatedly acquiring magnetic resonance data using the magnetic resonance imaging system during execution of the treatment plan. The instructions further cause the processor to perform the step of repeatedly calculating the temperature of the subject within the temperature measurement volume.

The instructions further cause the processor to perform the step of modifying the treatment plan during execution of the treatment in accordance with the temperature within the temperature measurement volume. This embodiment is particularly advantageous because the temperature within the temperature measurement volume is repeatedly measured or monitored using the magnetic resonance imaging system. As this is done during execution of the treatment plan modifications to the treatment plan may be performed on the fly to enhance the effectiveness or safety of executing the treatment plan.

In another embodiment the memory contains a pulse sequence for controlling the operation of the magnetic resonance imaging system. A pulse sequence as used herein is a set of commands or a timing diagram which is used to control the acquisition of magnetic resonance data using a magnetic resonance imaging system. The pulse sequence is an inversion recovery T2 weighted turbo spin echo or an inversion recovery T2 weighted spin echo pulse sequence. The pulse sequence is adapted for acquiring both transverse relaxometry data and longitudinal relaxometry data using an inversion time which is short in comparison to the T1 relaxation time. As used herein the longitudinal relaxation data encompasses magnetic resonance data which contains information which should be used to infer or calculate the T1 relaxation time. The T1 relaxation time referred to in this embodiment is the T1 relaxation time within the temperature measurement volume. This embodiment is advantageous because signal intensity changes due to temperature dependence of both T1 and T2 are additive which improves the sensitivity of the method.

In another embodiment the magnetic resonance data further comprises proton resonance frequency shift data. As used herein proton resonance frequency shift data encompasses magnetic resonance data which may use to determine the proton resonance frequency shift data which is dependent upon temperature. Execution of the instructions further cause the processor to perform the step of calculating the temperature of the subject within the temperature measurement volume in accordance with the proton resonance frequency shift data. It is advantageous because in addition to using the transverse relaxation relaxometry data and/or longitudinal relaxometry data to determine the temperature also the proton resonance frequency shift data may also be used to determine the temperature within the temperature measurement volume.

In another embodiment the memory contains a pulse sequence for controlling the operation of the magnetic resonance imaging system. The pulse sequence is automized during alternating time periods to attain the transverse relaxometry data and the proton resonance frequency shift data. This is advantageous because the pulse sequence may be modified such that these two different types of data are obtained both of which may be used for determining the temperature.

In another embodiment the temperature of each of the temperature measurement volumes is determined individually in accordance with any one of the following: the transverse relaxometry data and the proton resonance frequency shift data. If the longitudinal relaxometry data is available also then this may also be used to determine the temperature in the temperature measurement volume. This embodiment is advantageous because for different types of tissue different methods of determining a temperature may be beneficial. For instance for water or tissue containing mostly water the proton resonance frequency shift may provide an accurate measurement or determination of the temperature. However this is not necessarily in fatty tissue. In this case it may be beneficial to use the transverse relaxometry data to determine the temperature.

In another embodiment execution of the instructions causes the processor to perform the step of calculating the temperature of the subject within multiple temperature measurement volumes in accordance with the magnetic resonance data. Instead of just determining the temperature within a single temperature measurement volume the temperature within multiple volumes is determined.

In another embodiment execution of the instructions further causes the processor to perform the step of constructing a temperature map in accordance with the temperature measurement volumes. Since the temperature has been determined in multiple temperature measurement volumes a mapping of these various temperatures may be constructed. Execution of the instructions further causes the processor to perform the step of reconstructing a magnetic resonance image in accordance with the magnetic resonance data.

Execution of the instructions further causes the processor to perform the step of displaying a thermal magnetic resonance image on a display by superimposing the temperature map on the magnetic resonance image. This is particularly advantageous because the magnetic resonance image may display anatomical features and the temperature map may be used to map the temperature of these various anatomical features. This may be useful for an operator or physician to determine the effectiveness of a therapy using the apparatus or for manually altering the treatment plan during therapy.

In another embodiment the memory contains a pulse sequence for controlling the operation of the magnetic resonance imaging system. The pulse sequence is any one of the following: a turbo spin echo sequence, an echo planar imaging sequence, a spin echo pulse sequence, and a gradient echo sequence.

In another aspect the invention provides for a computer-implemented method of acquiring magnetic resonance thermometry data. The method comprises the step of acquiring magnetic resonance data using the magnetic resonance imaging system. The magnetic resonance data comprises transverse relaxometry data. The method further comprises the step of calculating the temperature of the subject within a temperature measurement volume in accordance with the transverse relaxometry data. The temperature measurement volume is within the imaging volume.

In another aspect the invention provides for a computer program product comprising machine executable instructions for execution by the processor of a computer system of an apparatus comprising a magnetic resonance imaging system. The computer program part may for instance be computer executable code stored on a computer-readable storage medium. Execution of the instructions causes the processor to perform the step of acquiring magnetic resonance data using the magnetic resonance imaging system. The magnetic resonance data comprises transverse relaxometry data. Execution of the instructions further cause the processor to perform the step of calculating the temperature of the subject within a temperature measurement volume in accordance with the transverse relaxometry data. The temperature measurement volume is within the imaging volume.

BRIEF DESCRIPTION OF THE DRAWINGS

In the following preferred embodiments of the invention will be described, by way of example only, and with reference to the drawings in which:

FIG. 1 shows a flow diagram which illustrates a method according to an embodiment of the invention;

FIG. 2 shows a flow diagram which illustrates a method according to a further embodiment of the invention;

FIG. 3 shows a functional diagram of an apparatus according to an embodiment of the invention;

FIG. 8 shows a timeline which may be used to illustrate how a Proton resonance frequency shift and T2 weighted pulse sequences may be integrated;

FIG. 9 shows an alternative method of integrating the proton resonance frequency shift and T2 weighted pulse sequences;

FIG. 10 shows a timeline which illustrates the interleaving of the proton resonance frequency shift pulse sequence with the T2 weighted pulse sequence and when heating is performed by the tissue heating system;

FIG. 11 shows a timing diagram of a gradient echo EPI pulse sequence which may be used for both proton resonance frequency shift and T2-star weighted imaging.

DETAILED DESCRIPTION OF THE EMBODIMENTS

Figure 4:
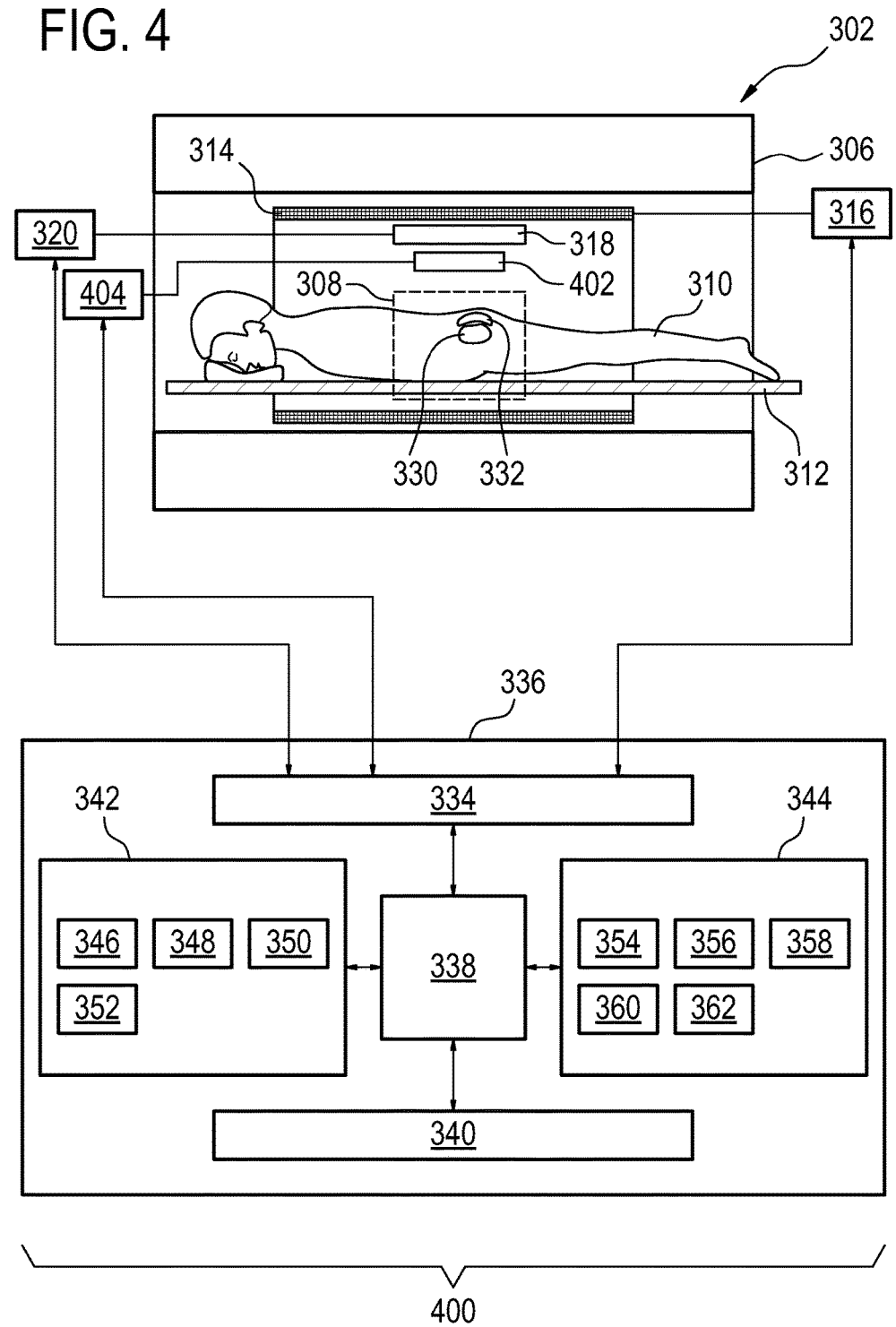
FIG. 4 shows a functional diagram of an apparatus according to a further embodiment of the invention.

Like numbered elements in these figures are either equivalent elements or perform the same function. Elements which have been discussed previously will not necessarily be discussed in later figures if the function is equivalent.

FIG. 1 shows a flow diagram which illustrates a method according to an embodiment of the invention. Step 100 magnetic resonance data is acquired which comprises transverse relaxometry data. In step 102 the temperature of a subject is calculated within a temperature volume in accordance with the transverse relaxometry data.

FIG. 2 shows a flow diagram which illustrates a method according to a further embodiment of the invention. In step 200 a treatment plan received which specifies a target volume. In step 202 the target volume is heated by the tissue heating system by executing the treatment plan. In step 204 magnetic resonance data is repeatedly acquired by the apparatus and the magnetic resonance data comprises transverse relaxometry data. In step 206 the temperature of a subject within a temperature volume is repeatedly calculated in accordance with the transverse relaxometry data. In step 208 the treatment plan is modified during execution of the treatment plan in accordance with the temperature that was repeatedly calculated.

FIG. 3 shows an embodiment of an apparatus 300 according to an embodiment of the invention. The apparatus 300 comprises a magnetic resonance imaging system 302 and a high intensity focused ultrasound system 304. The magnetic resonance imaging system 302 may be used to guide therapy using the high intensity focused ultrasound system 304.

The magnetic resonance imaging system 302 comprises a magnet 306. In this figure a cylindrical magnet with a bore through the center is shown. However other types of magnets may be used such as so-called open coil magnets or toroidal magnets. Within the bore of the magnet 306 there is an imaging volume 308 where the magnetic field is uniform enough for performing magnetic resonance imaging. A subject 310 is also located within the bore of the magnet 306 and a portion of the subject 310 is within the imaging volume 308. The subject 310 is reposing on a subject support 312. Also within the bore of the magnet is a magnetic field gradient coil 314. The magnetic field gradient coil 314 is connected to a magnetic field gradient coil power supply 316 which supplies current to the magnetic field gradient coil 314. Adjacent to the imaging volume 308 is a radio frequency coil 318. The radio frequency coil 318 is connected to a radio frequency transceiver 320.

The high intensity focused ultrasound system 304 comprises an ultrasound transducer 322 which is immersed in a fluid filled chamber 324. Not shown in this figure is a power supply for supplying power to the ultrasound transducer 322. There may also be a mechanism for physically moving the ultrasound transducer 322 in some embodiments. The fluid filled chamber 324 is for good coupling of ultrasound energy to the subject 310. The fluid filled chamber 324 has a ultrasound window 325 which seals it but however it allows ultrasound to pass through. The subject support 312 has an opening with which a gel pad 327 has been placed on the ultrasound window 325. The gel pad 327 provides ultrasound coupling between the ultrasound window 325 and the subject 310. The dotted lines 326 show the rough direction of travel of the focused ultrasound towards a sonication zone 328 within the subject 310. The sonication zone 328 is shown as being within target zone 330. In the course of a therapy focused ultrasound is generated in the sonication zone 328 which heats the target zone 330. Adjacent to the target zone 330 is a temperature measurement volume 332. The magnetic resonance imaging system 302 is used to monitor the temperature in the temperature measurement volume 332.

The high intensity focused ultrasound system 304 the radio frequency transceiver 320 and the magnetic field gradient coil power supply 316 are all connected to a hardware interface 334 of a computer system 336. The computer system 336 is used to control the apparatus 300 and comprises a processor 338. The processor 338 is connected to the hardware interface 334 and a user interface 340. The user interface comprises devices which an operator may use to interact with the computer system 336. For instance the hardware interface may comprise a mouse, a keyboard and a display. Images which are rendered by the computer system 336 may be displayed on a display of the user interface 340. The processor 338 is further shown as being connected to a computer storage 342 and a computer memory 344.

The computer storage 342 is shown as containing magnetic resonance data 346 that has been acquired by the magnetic resonance imaging system 302. The computer storage 342 further comprises a magnetic resonance imaging image which has been reconstructed from the magnetic resonance data 346. The computer storage 342 further contains a treatment plan 350. The computer storage 342 further contains a pulse sequence 352 which contains a timing diagram which is used for operating the magnetic resonance imaging system 302. Computer memory 344 as shown as containing a magnetic resonance imaging control module. The magnetic resonance imaging control module 354 contains computer executable code for controlling the operation of the magnetic resonance imaging system 302. The magnetic resonance imaging control module 354 uses the pulse sequence 352 for generating control commands for the magnetic resonance imaging system 302.

The computer memory 344 further contains a tissue heating system control module 356. The tissue heating system control module 356 contains executable instructions for controlling the operation of the tissue heating system 304. In other embodiments the tissue heating system control module 356 contains codes for operating different types of tissue heating systems. The computer memory 344 further contains a temperature calculation module 358. The temperature calculation module contains computer executable code which uses the magnetic resonance data 346 to calculate a temperature of the temperature measurement volume 332. The memory 344 is further shown as containing a treatment plan modification module 360. The treatment plan modification module 360 contains computer executable code which uses the value of the temperature of the temperature measurement volume 332 as an input to modify the treatment plan 350. The computer memory 344 is shown as further containing an image reconstruction module 362. The image reconstruction module contains computer executable code which is able to generate the magnetic resonance imaging image 348 using the magnetic resonance data 346.

FIG. 4 shows an apparatus 400 according to a further embodiment of the invention. The apparatus 400 shown in FIG. 4 is very similar to the apparatus shown in FIG. 3. Instead of using a high intensity focused ultrasound system the target volume 330 is heated using a radio frequency coil 402 and a radio frequency generator 404. The target zone 402 is essentially heated with radio frequency energy. As with the previous embodiment the temperature within the temperature measurement volume 332 is measured using the magnetic resonance imaging system 302. In this embodiment the tissue heating system control module 356 is used for controlling the radio frequency generator 404.

Figure 5:
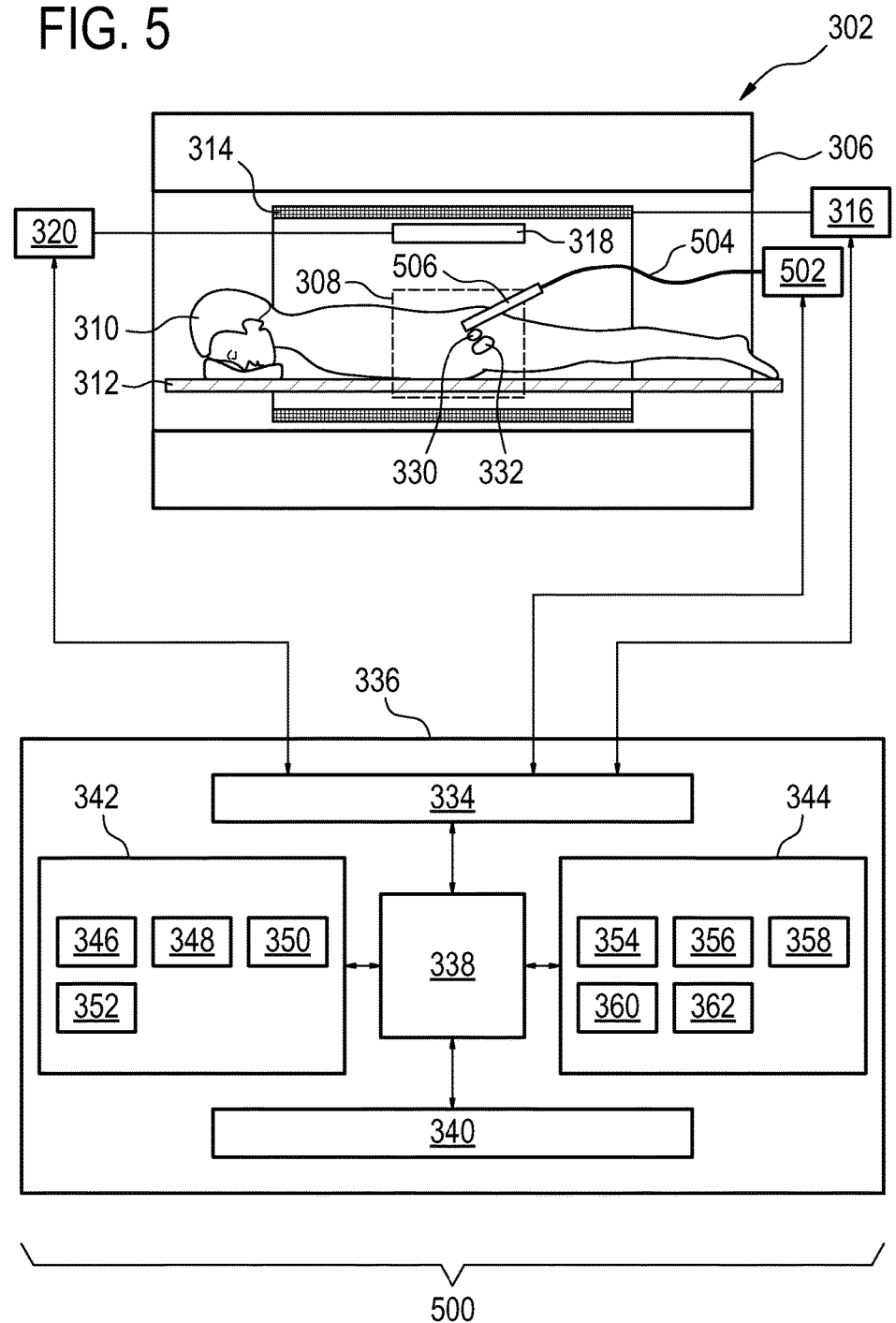
FIG. 5 shows a functional diagram of an apparatus according to a further embodiment of the invention.

FIG. 5 shows an apparatus 500 according to a further embodiment of the invention. The apparatus 500 shown in FIG. 5 is similar to the apparatuses shown in FIGS. 3 and 4. In the embodiment shown in FIG. 5 a laser 502 is used to heat the target zone 330 instead. There is a laser 502 which is controlled by the processor 338 via hardware interface 334. The laser 502 is connected to a laser catheter 506 via a fiber optic 504. The laser catheter 506 is inserted invasively into the subject 310. The laser catheter 506 is used to focus and ablate tissue in the target zone 330. The magnetic resonance imaging system 302 is used to monitor the temperature 332 in the temperature measurement volume 332. In this embodiment the tissue heating system control module 356 is used for controlling the laser 502.

Figure 6:
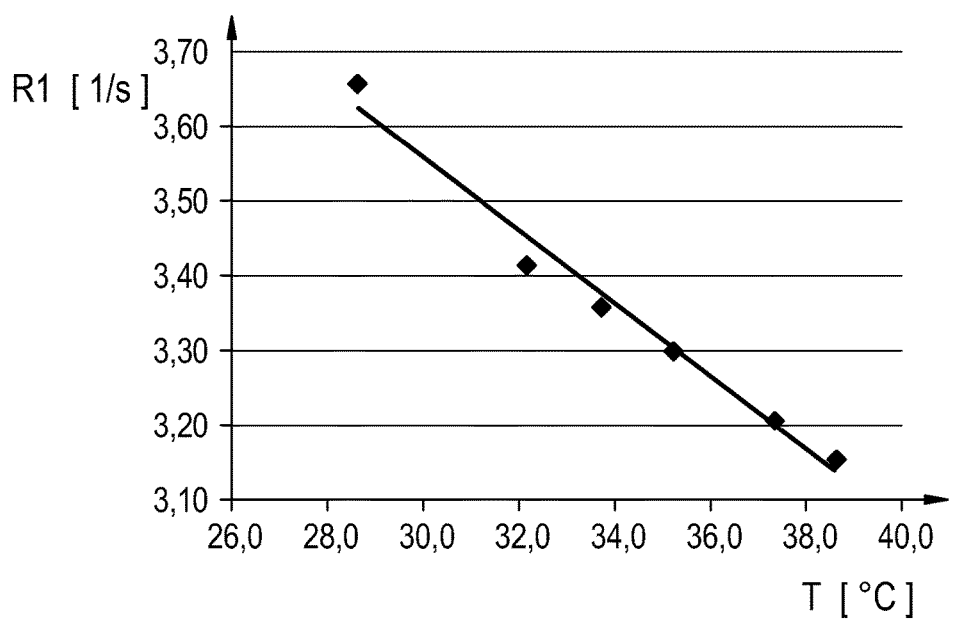
FIG. 6 shows a plot which illustrates how temperature may be determined using the value of the T1 relaxation rate.

FIG. 6 shows a plot which illustrates how the temperature in the temperature measurement volume may be determined using the value of the T1 relaxation rate. Performance measurement an in-vitro fat sample was warmed in a water bath within a magnetic resonance imaging system. Thermocouples were used to measure the actual temperature of the fat sample. The T1 value was measured with a IR pulse sequence. The X axis is the temperature in degrees Celsius. The Y axis is the R1 value. The R1 value is one over the T1 relaxation rate. Points are measured values and the solid line is a linear fit to the data. The plot in FIG. 6 illustrates that the T1 value may be used for measuring the temperature of fat using magnetic resonance imaging.

Figure 7:
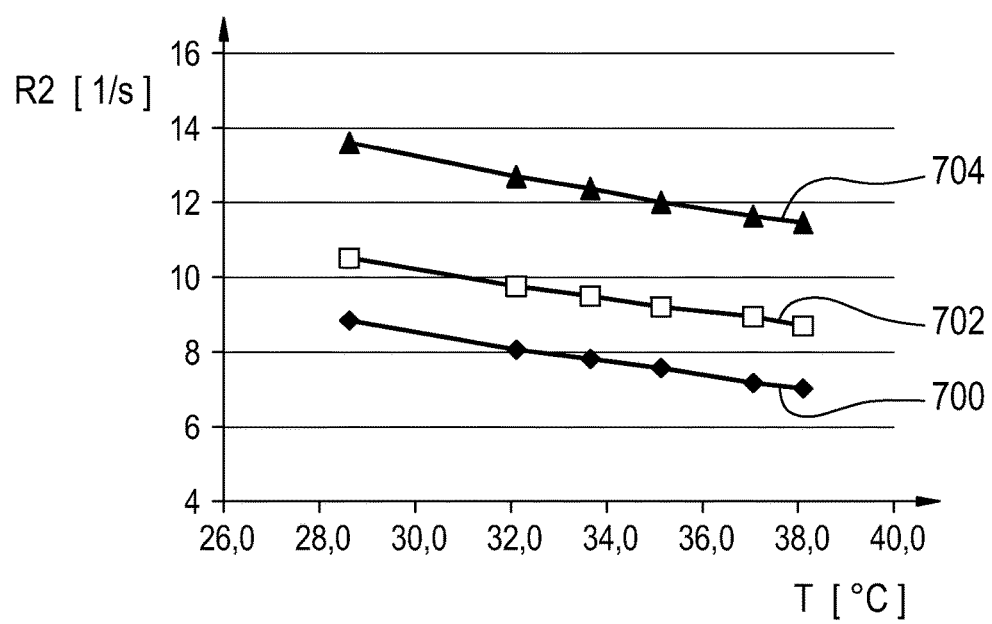
FIG. 7 shows a plot which illustrates how the T2 relaxation rate may be used to determine the temperature of fat or fatty tissue.

FIG. 7 shows a plot which illustrates how the T2 relaxation rate may be used to govern the temperature of fat or fatty tissue using magnetic resonance imaging. The T2 values shown in this plot were measured using SE and TSE pulse sequences. There are inter-echo spacings of 5, 13, and 20 milliseconds respectively. As with FIG. 6 the X axis shows the temperatures in degrees Celsius. The Y axis shows the R2 value. R2 is one over the T2 value. There are three sets of data shown in FIG. 10. The points and line labeled 700 correspond to the five milliseconds inter-echo spacing. The points are the actual data and the line is the linear fit. The same is shown with the line and points labeled 702. The line and points labeled 702 are for 13 milliseconds. The line and points labeled 704 are for 20 milliseconds for the value of the echo spacing.

FIG. 8 shows a timeline which may be used to illustrate how a Proton Resonance Frequency shift (PRF) and T2 weighted (T2W) pulse sequences may be integrated. The regions labeled 800 are when a pulse sequence which can measure the PRF or proton resonance frequency shift can be measured. The sections of the timeline labeled 802 represent when a pulse sequence which acquires data which may be used to determine the T2 relaxation rate is measured.

One possible timing of interleaving PRF and T2 weighted sequences. N1 slices are obtained with PRF sequence, after which after N2 slices (may be partly the same or completely different slices as with PRF) with T2w (or T2w-star) sequence, where N1 is a predetermined number of slices and N2 is a second predetermined number of slices. After that, N1 slices with PRF is obtained and so on. In this arrangement both sequences are updated with the same interval, i.e. temperature information of both sequences has the same temporal resolution.

FIG. 9 shows an alternative method of interleaving the PRF and T2 weighted pulse sequences. The sections of the timeline labeled 900 are when the PRF pulse sequence is performed. The section of the timeline labeled 902 is when the T2 weighted pulse sequence is performed.

One possible timing of interleaving PRF and T2 weighted (T2w) sequences. T2w-star is an abbreviation for a T2-star weighted image. PRF sequence is repeated N times, after which T2w (or T2w-star) sequence is obtained. After that, PRF is obtained again N times etc. In this arrangement PRF image is updated more often than T2w image. Yet another modification is to collect only part of the k-space in each time period to further adjust the image quality vs. temporal resolution point.

FIG. 10 shows a timeline which illustrates the interleaving of the PRF pulse sequence with the T2 weighted pulse sequence along with when heating is performed by the tissue heating system. The sections of the timeline labeled 1000 are when the PRF pulse sequence is performed. The section of the timeline labeled 1002 are when the T2W pulse sequence is performed. Initially it is seen that a reference measurement 1004 is performed before the heating 1006 is activated. Reference measurement 1004 is to take a baseline measurement. After the heating 1006 is activated additional PRF pulse sequences and T2W pulse sequences are performed to measure heating during the heating process.

Timing diagram showing how one or more reference images are obtained before switching on the heating device (e.g. focused ultrasound).

FIG. 11 shows a timing diagram of a gradient echo EPI pulse sequence which may be used for both PRF and T2W-star imaging. The timing diagram for the RF is labeled 1100. The gradient slice is labeled 1102. The gradient phase is labeled 1104 and the gradient read is labeled 1106. The timed repetition is indicated by a bar labeled 1108. The time to echo is represented by a bar labeled 1110. The bracket 1112 indicates that this pulse sequence is repeat n times. Corresponding echoes are labeled E1 through En.

Timing diagram of gradient echo EPI sequence which can be used both for PRF and T2w-star imaging. Effective echo time TE (essentially referring to the echo where the center of the k-space is acquired) defines the sensitivity of the sequence o for both purposes. The sequence can be either single shot, when all the phase encodings are collected after a single excitation (alpha) pulse, or multishot, when part of the encodings are collected and the sequence is then repeated with different phase encodings.

Figure 12:
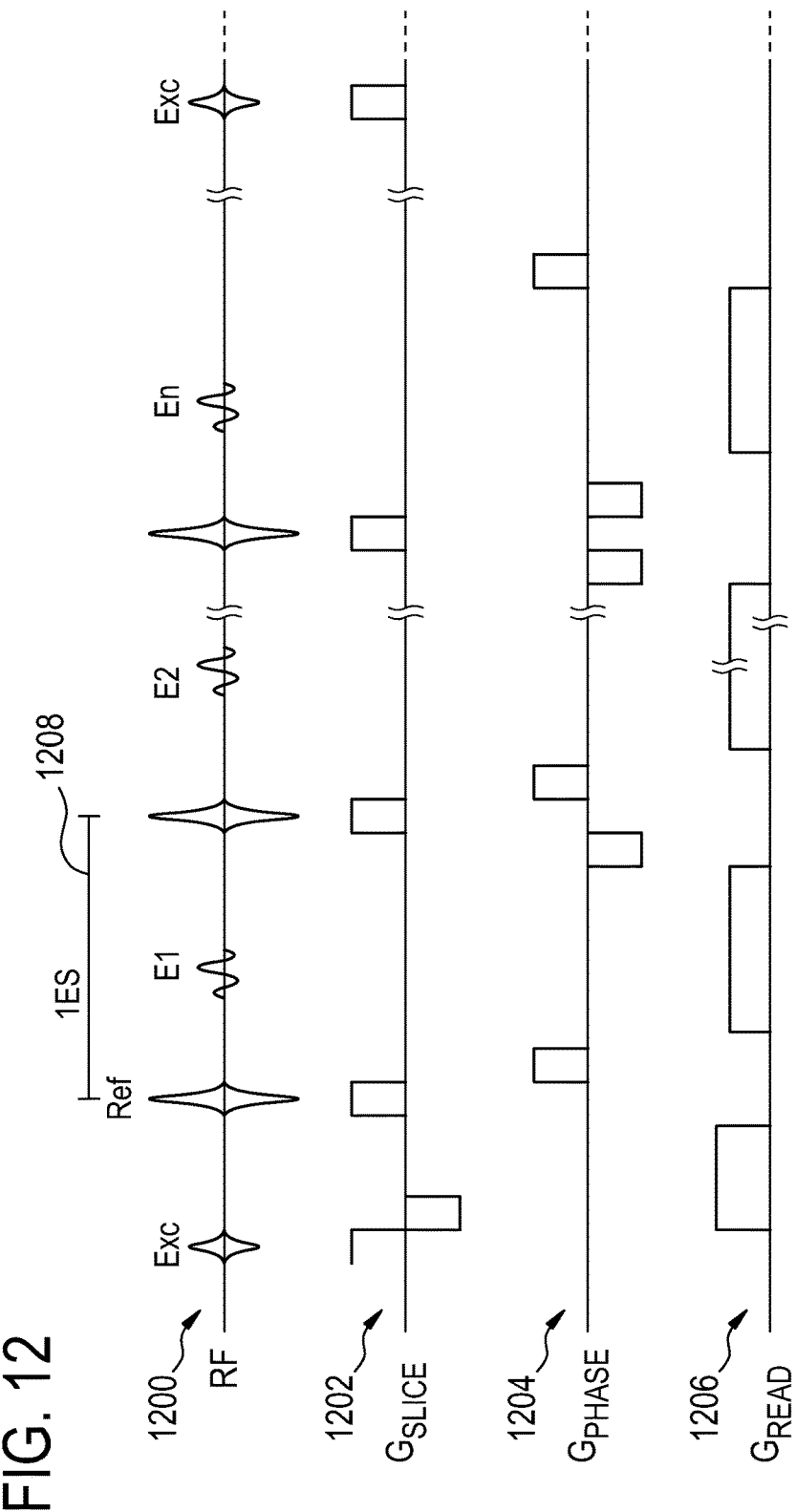
FIG. 12 shows a diagram for a turbo spin echo pulse sequence which can be used for T2 weighted imaging.

FIG. 12 shows a diagram for a turbo spin echo pulse sequence which can be used for both T2W imaging. The bar labeled 1200 shows the RF timing. The bar labeled 1202 shows the timing for the G slice parameter. 1204 shows the value for G phase. 1206 shows the value for G read. The bar labeled 1208 represents the inter-echo spacing or IES. The bar labeled 1112 indicates that the reading of the echoes is performed N times. Corresponding echoes are labeled E1 through En.

As was mentioned before, FIG. 12 shows a timing diagram of turbo spin echo (TSE) sequence which can be used both for T2w imaging. Effective Echo Time (TE) (essentially referring to the echo where the center of the k-space is acquired) defines the sensitivity of the sequence for the purpose. The sequence can be either single shot, when all the phase encodings are collected after a single excitation pulse, or multishot, when part of the encodings are collected and the sequence is then repeated with different phase encodings. Inter Echo spacing (IES) affects on the sensitivity of the sequence to J-coupling effect. There is a modification of the sequence where two (or, in principle, even more) images with different effective echo times are produced. This would allow quantitative estimation of T2.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 first item
300 apparatus
302 magnetic resonance imaging system
304 high intensity focused ultrasound system
306 magnet
308 imaging volume
310 subject
312 subject support
314 magnetic field gradient coil
316 magnetic field gradient coil power supply
318 radio frequency coil
320 radio-frequency transceiver
322 ultrasound transducer
324 fluid filled chamber
325 ultrasound window
326 path of ultrasound
327 gel pad
328 sonication zone
330 target zone
332 temperature measurement volume
334 hardware interface
336 computer system
338 processor
340 user interface
342 computer storage
344 computer memory
346 magnetic resonance data
348 magnetic resonance imaging image
350 treatment plan
352 pulse sequence
354 magnetic resonance imaging control module
356 tissue heating system control module
358 temperature calculation module
360 treatment plan modification module
362 image reconstruction module
400 apparatus
402 radio-frequency coil
404 radio-frequency generator
500 apparatus
502 laser
504 fiber optic
506 laser catheter
700 5 ms
702 13 ms
704 20 ms
800 PRF pulse sequence performed
802 T2W pulse sequence performed
900 PRF pulse sequence performed
902 T2W pulse sequence performed
1000 PRF pulse sequence performed
1002 T2W pulse sequence performed
1004 reference measurement
1006 heating performed

The invention claimed is:

1. An apparatus comprising a magnetic resonance imaging system, the magnetic resonance imaging system comprising:
    a magnet adapted for generating a magnetic field for orientating the magnetic spins of nuclei of a subject located within an imaging volume;
    a radio frequency transceiver adapted for acquiring magnetic resonance data using a radio frequency coil;
    a magnetic field gradient coil adapted for spatial encoding of the magnetic spins of nuclei within the imaging volume;
    a magnetic field gradient coil power supply adapted for supplying current to the magnetic field gradient coil;
    a computer system comprising a processor, wherein the computer system is adapted for controlling the apparatus; and
    a memory containing machine readable instructions for execution by the processor, wherein execution of the instructions cause the processor to perform the steps of:
        acquiring magnetic resonance data using the magnetic resonance imaging system, wherein the magnetic resonance data comprises transverse relaxometry T2 data, as well as proton resonance frequency shift data, wherein at least the transverse relaxometry T2 data is acquired using a turbo spin echo (TSE) sequence, and
        calculating temperature of the subject within a temperature measurement volume during therapeutic treatment in accordance with the transverse relaxometry T2 data, in combination with calculating the temperature of the subject within the temperature measurement volume in accordance with the proton resonance frequency shift data, wherein the temperature measurement volume is within the imaging volume.

2. The apparatus of claim 1, wherein the machine readable instructions include to interleave the acquisition of the transverse relaxometry data with the acquisition of the proton resonance frequency shift data.

3. The apparatus of claim 2, wherein the machine readable instructions include to repeatedly measure or monitor the temperature and to update the proton resonance frequency shift data more often than transverse relaxometry data.

4. The apparatus of claim 1, wherein the acquisition of the transverse relaxometry data involves a fat-selective excitation and the temperature measurement in accordance with the proton resonance frequency shift data involves a water-selective excitation.

5. The apparatus of claim 1 in which the acquisition of the transverse relaxometry data involves a repetition time that is longer than longitudinal relaxation time (T1) of the same tissue in the measurement volume.

6. The apparatus of claim 1, further comprising a tissue heating system for heating a target volume of the subject during the therapeutic treatment, wherein the target volume is within the imaging volume, and wherein the computer system is further adapted for controlling the tissue heating system.

7. The apparatus of claim 6, wherein the tissue heating system comprises one of the following: a high intensity focused ultrasound system for sonicating the target volume, a radio frequency tissue heating system for heating the target volume with radio frequency energy, and a laser ablation system for ablating tissue within the target volume.

8. The apparatus of claim 6, wherein the instructions further cause the processor to perform the steps of:
receiving a treatment plan specifying the target volume within the imaging volume, wherein the treatment plan comprises instructions for controlling operation of the tissue heating system;
heating the target volume using the tissue heating system by executing the treatment plan;
acquiring repeatedly magnetic resonance data using the magnetic resonance imaging system during execution of the treatment plan;
calculating repeatedly the temperature of the subject within the temperature measurement volume; and
modifying the treatment plan during execution of the treatment in accordance with the temperature within the temperature measurement volume.

9. The apparatus of claim 1, wherein the memory contains a pulse sequence for controlling operation of the magnetic resonance imaging system, wherein the pulse sequence is an inversion recovery T2 weighted turbo spin echo sequence, and wherein the pulse sequence is adapted for acquiring both longitudinal relaxometry T1 data and the transverse relaxometry T2 by using an inversion time which is shorter than T1 relaxation time.

10. The apparatus of claim 1, wherein execution of the instructions further causes the processor to perform the steps of:
constructing a temperature map in accordance with the temperature measurement volumes;
reconstructing a magnetic resonance image in accordance with the magnetic resonance data; and
displaying a thermal magnetic resonance image on a display by superimposing the temperature map on the magnetic resonance image.

11. A computer-implemented method of acquiring magnetic resonance thermometry data, the method comprising the steps of:
acquiring magnetic resonance data using a magnetic resonance imaging system to implement a turbo spin echo (TSE) sequence, wherein the magnetic resonance data comprises transverse relaxometry T2 data as well as proton resonance frequency shift data, and
calculating temperature of a subject within a temperature measurement volume during therapeutic treatment in accordance with the transverse relaxometry T2 data in combination with calculating the temperature of the subject within the temperature measurement volume in accordance with the proton resonance frequency shift data, wherein the temperature measurement volume is within an imaging volume of the magnetic resonance imaging system.

12. A computer program product having a non-transitory computer readable memory comprising machine executable instructions for execution by a processor of a computer system of an apparatus comprising a magnetic resonance imaging system;
wherein execution of the instructions cause the processor to perform the steps of:
acquiring magnetic resonance data using the magnetic resonance imaging system to implement a turbo spin echo (TSE) sequence, wherein the magnetic resonance data comprises transverse relaxometry T2 data as well as proton resonance frequency shift data; and calculating temperature of a subject within a temperature measurement volume in accordance with the transverse relaxometry T2 data in combination with calculating the temperature of the subject within the temperature measurement volume during therapeutic treatment in accordance with the proton resonance frequency shift data, wherein the temperature measurement volume is within an imaging volume of the magnetic resonance imaging system.

* * * * *